(12) United States Patent
DiFoggio et al.

(10) Patent No.: US 7,084,392 B2
(45) Date of Patent: Aug. 1, 2006

(54) METHOD AND APPARATUS FOR A DOWNHOLE FLUORESCENCE SPECTROMETER

(75) Inventors: Rocco DiFoggio, Houston, TX (US); Arnold Walkow, Houston, TX (US); Paul Bergren, Houston, TX (US); Louis Perez, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 207 days.

(21) Appl. No.: 10/641,327

(22) Filed: Aug. 14, 2003

(65) Prior Publication Data

US 2004/0104355 A1    Jun. 3, 2004

Related U.S. Application Data

(63) Continuation-in-part of application No. 10/453,717, filed on Jun. 3, 2003.

(60) Provisional application No. 60/385,633, filed on Jun. 4, 2002.

(51) Int. Cl.
*G01V 5/08* (2006.01)
(52) U.S. Cl. .................. 250/269.1; 250/302; 250/461.1
(58) Field of Classification Search ................ 250/302, 250/269.1, 461.1
See application file for complete search history.

(56) References Cited

U.S. PATENT DOCUMENTS

| | | | |
|---|---|---|---|
| 4,814,614 A * | 3/1989 | Tsui | .......................... 250/301 |
| 5,049,738 A | 9/1991 | Gergely et al. | |
| 5,166,747 A | 11/1992 | Schroeder et al. | |
| 5,762,419 A | 6/1998 | Yam | |
| 5,912,459 A | 6/1999 | Mullins et al. | |
| 5,965,896 A | 10/1999 | Marton | |
| 6,008,055 A | 12/1999 | Zhu et al. | |
| 6,016,191 A | 1/2000 | Ramos et al. | |
| 6,023,340 A | 2/2000 | Wu et al. | |
| 6,069,694 A | 5/2000 | VonBargen | |
| 6,075,595 A | 6/2000 | Malinen | |
| 6,075,611 A | 6/2000 | Dussan V. et al. | |
| 6,140,637 A | 10/2000 | Mullins et al. | |
| 6,268,603 B1 | 7/2001 | Mullins et al. | |

(Continued)

FOREIGN PATENT DOCUMENTS

WO    WO 92/07249    4/1992

(Continued)

OTHER PUBLICATIONS

A.R. Smits et al., "In-Situ Optical Fluid Anaylsis As An Aid To Wireline Formation Sampling", SPE Formation Evaluation, Jun. 1995, pp. 91-98.

Primary Examiner—David Porta
Assistant Examiner—Christopher Webb
(74) Attorney, Agent, or Firm—Madan, Mossman & Sriram, P.C.

(57) ABSTRACT

The invention comprises an apparatus and method for simple fluorescence spectrometry in a downhole environment using a UV light source and UV fluorescence to determine a parameter of interest for a sample downhole. The UV light source illuminates the fluid, which in turn fluoresces light. The fluoresced light is transmitted back towards the UV light source and through the pathway towards an optical spectrum analyzer. API gravity is determined by correlation the wavelength of peak fluorescence and brightness of fluorescent emission of the sample. Asphaltene precipitation pressure is determined by monitoring the blue green content ratio for a sample under going depressurization.

33 Claims, 4 Drawing Sheets

U.S. PATENT DOCUMENTS

| | | | |
|---|---|---|---|
| 6,274,865 B1 * | 8/2001 | Schroer et al. | 250/269.1 |
| 6,321,839 B1 | 11/2001 | Vereecken et al. | |
| 6,420,869 B1 | 7/2002 | DiFoggio | |
| 6,476,384 B1 * | 11/2002 | Mullins et al. | 250/269.1 |
| 6,501,072 B1 * | 12/2002 | Mullins et al. | 250/256 |
| 6,529,543 B1 | 3/2003 | Anderson et al. | |
| 6,678,050 B1 | 1/2004 | Pope et al. | |
| 6,704,109 B1 | 3/2004 | Wu et al. | |
| 6,729,400 B1 * | 5/2004 | Mullins et al. | 166/264 |
| 6,743,221 B1 | 6/2004 | Hobart et al. | |
| 6,768,105 B1 | 7/2004 | Mullins et al. | |
| 2001/0023614 A1 | 9/2001 | Tubel et al. | |
| 2002/0070681 A1 * | 6/2002 | Shimizu et al. | 315/246 |
| 2002/0118905 A1 | 8/2002 | Wu et al. | |
| 2002/0159101 A1 * | 10/2002 | Alderson et al. | 358/504 |
| 2002/0176646 A1 | 11/2002 | Wu et al. | |
| 2003/0029995 A1 | 2/2003 | Mullins et al. | |
| 2004/0000636 A1 * | 1/2004 | Mullins et al. | 250/269.1 |

FOREIGN PATENT DOCUMENTS

| | | |
|---|---|---|
| WO | WO 01/20322 | 3/2001 |
| WO | WO 01/20322 A1 | 3/2001 |
| WO | WO 200120322 A1 * | 3/2001 |

* cited by examiner

METHOD AND APPARATUS FOR A DOWNHOLE FLUORESCENCE SPECTROMETER

CROSS-REFERENCE TO RELATED APPLICATIONS

This patent application is a continuation in part of and takes priority from U.S. patent application Ser. No. 10/453,717 filed on Jun. 3, 2003 entitled "A Method and Apparatus for a Downhole Fluorescence Spectrometer" by DiFoggio et al. This patent application also takes priority from U.S. Provisional Patent Application Ser. No. 60/385,633 filed on Jun. 4, 2002 entitled "A Method and Apparatus for a Downhole Fluorescence Spectrometer" by DiFoggio et al. This application is related to U.S. patent application Ser. No. 10/162,023, entitled "A Method and Apparatus for a High Resolution Downhole Spectrometer" by Rocco DiFoggio, Paul Bergen and Arnold Walkow, filed on Jun. 4, 2002 which is hereby incorporated herein by reference in its entirety. This application is related to U.S. patent application Ser. No. 10/162,030, entitled "A Method and Apparatus for a Derivative Spectrometer" by Rocco DiFoggio, Paul Bergen and Arnold Walkow, filed on Jun. 4, 2002 which is hereby incorporated herein by reference in its entirety. This application is related to the U.S. patent application Ser. No. 10/119,492 filed on Apr. 10, 2002 by Rocco DiFoggio et al., entitled "A Method and Apparatus for Downhole Refractometer And Attenuated Reflectance Spectrometer" which is hereby incorporated herein by reference in its entirety.

BACKGROUND OF THE INVENTION

1. Field of the Invention

The present invention relates to an apparatus and method for performing simple fluorescence spectrometry using a UV LED light source in a downhole environment to estimate sample clean up and API gravity based on the spectral response over time. Tracers are added to enhance detection of oil and water based mud.

2. Background of the Related Art

Fluorescence analysis has been performed on cuttings or cores obtained during the drilling of wells to determine the presence of hydrocarbons in pore fluid. An example of such a technique can be found in U.S. Pat. No. 4,690,821. In techniques such as these, cuttings or cores are cleaned to remove any drilling fluid products, which might otherwise interfere with the analysis. The samples are crushed and extracted with a solvent, which is then analyzed. Alternatively the sample is irradiated directly and the fluorescence analyzed. While this technique can provide reasonably accurate analysis of the pore fluids, there are certain drawbacks. Cores are relatively expensive to obtain and must be returned to the surface for analysis. Also, since cores are only taken from specific locations, it is possible that hydrocarbon-bearing formation can be overlooked. Cuttings are obtained continuously in drilling, but have the disadvantage that it is not possible to determine at the surface exactly where the cuttings originate downhole, making the identification of hydrocarbon-bearing formations difficult. Also, cuttings give no accurate indication of the extent of any hydrocarbon bearing formations. Recent innovations have concentrated on performing fluorescence experiments in a downhole environment.

U.S. Pat. No. 5,912,459 by Mullins et al. titled Method And Apparatus For Fluorescence Logging discloses a method comprising illuminating a borehole with light from a source within a tool and detecting any fluorescent radiation with a detector in the tool and analyzing the fluorescent radiation to determine the presence of hydrocarbon in the formation. Preferably, the borehole wall is illuminated and fluorescence detected through a window in the tool which is pressed against the borehole wall. The window is typically pressed against the borehole wall with sufficient force to displace any mudcake for a substantial time, as the tool is moved through the borehole. Pressing the window against the borehole wall minimizes rugosity effects, assuming low rugosity.

PCT application (International Publication Number WO 01/20322 A1) discloses a method of fluorescence spectrometry for predicting the asphaltene precipitation onset pressure in a downhole formation. The invention of this patent comprises illuminating and measuring an isolated sample at several pressures. As asphaltenes precipitate, they induce significant optical scattering. Asphaltene precipitation is detected as a sharp reduction of transmitted light and a large increase in the light scattering strength of the sample. WO 01/20322 teaches fluorescence as a determination of contaminants only. Thus, there is a need for a method and apparatus for determining oil properties and to further oil sample purity using fluorescence.

A downhole environment is a difficult one in which to operate a sensor. Measuring instruments in a downhole environment need to work under conditions of limited space within a tool's pressure housing, at elevated temperatures, and they need to withstand shock and vibration. Thus, there is a need for a simple but robust fluorescence spectrometer suitable for operation in a downhole environment.

SUMMARY OF THE INVENTION

The present invention provides a UV LED or an array of small LEDs for a UV light source. The array of small LEDs is more electrically efficient than a single larger LED. The present invention enable monitoring sample cleanup (change in fluorescence) as synthetic Oil Based Mud (OBM) filtrate has no aromatics so it does not fluoresce but crude oil has aromatics which do fluoresce.

A preferable UV LED had a Gallium Nitride (GaN) active layer, an aluminum nitride (AlN) buffer layer (also called cladding), and a sapphire substrate. A poorer performing UV LED had a Gallium Nitride (GaN) active layer, an aluminum indium nitride (AlInN) buffer layer, and a silicon carbide substrate.

The present invention also enables estimating additional crude oil properties downhole because a brighter and/or bluer measured fluorescence indicates a higher API gravity. Upon depressurizing a live crude oil, the ratio of blue to green fluorescence changes upon passing below the asphaltene precipitation pressure.

The present invention also provides fluorescent tracer applications in which adding a tracer to mud enables added enhanced measurements to distinguish between oil and OBM filtrate to help quantify OBM filtrate contamination based on the presence or absence of tracers.

For more quantitative results, we are correcting the raw fluorescence response using a formula for each channel which consists of three factors, The present invention also provides for correlation of raw measurement data as follows: Ch_X_Multiplicative_Correction_Factor_at_Temperature_T=(Correction Factor for Dimming of a UV LED Light Source, that is being run at Constant Current, as the Temperature Increases)* (Correction Factor for the Reduction in Photodiode Signal with Increasing Temperature for the Same Illumination Level)* (Correction Factor for Differences in Amplifier Gains between Channels, Differences in Photodiode Sensitivity, and Changes in Sensitivity with Temperature)

The present invention comprises an apparatus and method for performing simple fluorescence spectrometry in a downhole environment. The apparatus can be attached to a downhole fluid characterization module, that is already in use. The apparatus comprises a UV light source comprising two UV light bulbs, an UV LED or an array of smaller UV LEDS, an optically clear UV coupler or light pipe and a fluid containment system for containing a sample under analysis. The optically clear UV coupler and fluid containment system are made of sapphire. The fluid containment system already exists as part of the Baker Atlas SampleViews$^{SM}$ RCI tool. The apparatus of the present invention is attached in a manner that enables light transmitted by a light source on the far side of the fluid containment system to pass through a pathway in a plate holding the UV light source. UV light illuminates the fluid, which in turn fluoresces. The fluoresced light from the sample is transmitted back towards the UV bulb mount and through the light pipe pathway towards an optical spectrum analyzer for analysis.

In one embodiment of the invention, an operator monitors crude-oil sample cleanup over time by observing the rising and leveling off of a series of samples fluorescence over time. In another embodiment of the invention, an operator estimates crude oil properties from fluorescence-ratio models, which are not sensitive to dilution by a non-fluorescing liquid, such as the filtrate of synthetic mud. A processor is provided to host a chemometric equation or neural network for prediction of a fluid property based on the measured fluorescence spectrum. In another embodiment the API gravity is estimated based on correlation between measured fluorescence brightness and blue content. In another embodiment the OBM filtrate contamination is estimated by adding a tracer to OBM that fluorescences at a color, e.g. red, at which crude oil does not fluoresce to distinguish between crude oil and filtrate by detecting red fluorescence.

DETAILED DESCRIPTION OF A PREFERRED EMBODIMENT

Figure 1:
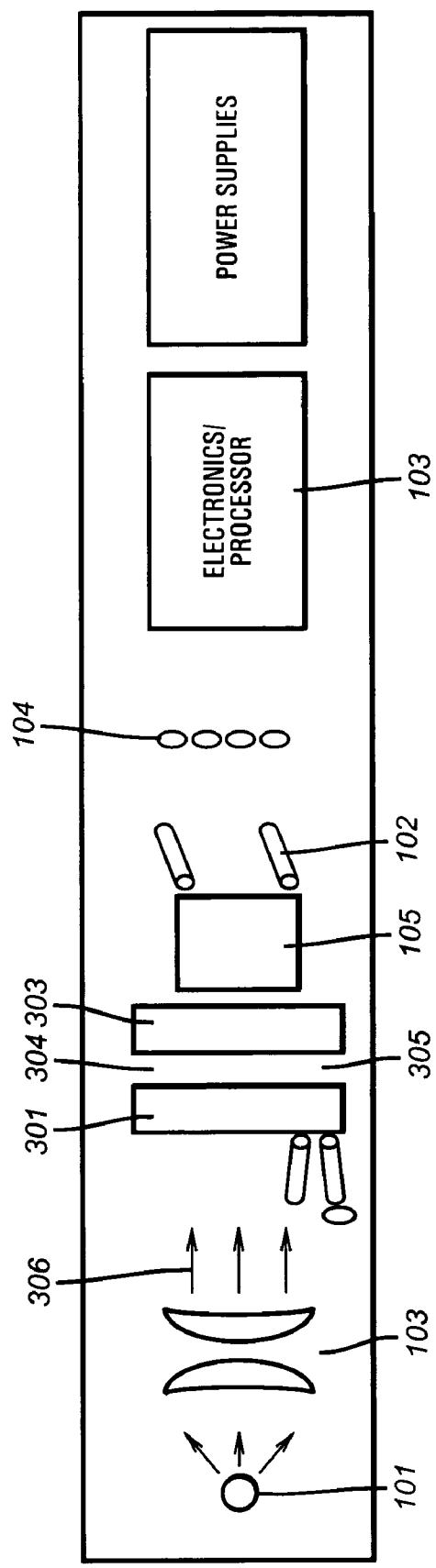
FIG. 1 is a diagram of the Fluid Characterization Module SampleViews$^{SM}$.

FIG. 1 illustrates the existing space layout within a downhole fluid characterization module, as, for example, the Baker Atlas SampleViews$^{SM}$ RCI tool. A white light source 101 (e.g. tungsten light bulb) emits light toward a sample, and a collimating lens device 103 is positioned between the white light source 101 and the sample collimates this light. The collimated light is incident generally perpendicular to a first sapphire window 301. Sapphire windows 301 and 303 lie generally perpendicular to the collimated beam of light 306 and are separated by a gap or channel 304 enabling a fluid sample 305 to flow between them. Reflected and fluoresced light can be used to determine sample properties. The existing downhole tools (FIG. 1) are fitted with a UV light source 102, which can be turned on when the tungsten light source 101 is turned off. The UV light source comprises one or more UV bulbs, an UV LED or an array of small UV LEDs. A spectrometer 104, comprising single wavelength filters over photodiodes, enables measuring and collecting the crude oil fluorescence measurement data. Electronics/processor 308 acquire and process the output of the photodiodes. The depth of investigation in the sample is only 1–2 microns from the sapphire window surface into the sample, thus the optical measurements for the sample are not affected by gas bubbles or particles more than 3 microns from the window surface. The narrow depth of investigation is referred to as an interface technique because only a very shallow depth (1–2 microns) is investigated in the sample. Thus, the interface technique provided by the present invention substantially eliminates temporary increases in brightness caused by a gas bubbles and temporary increases in darkness caused by particles as most all bubbles and particles do not pass within 1–2 microns of the sapphire window surface.

Figure 2B:
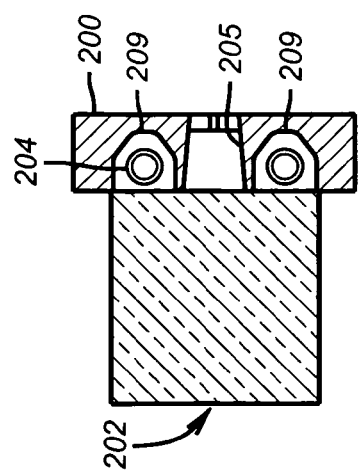
FIG. 2 is a diagram of the components to add this ultra-violet light source to a spectral analysis unit.
Figure 2A:
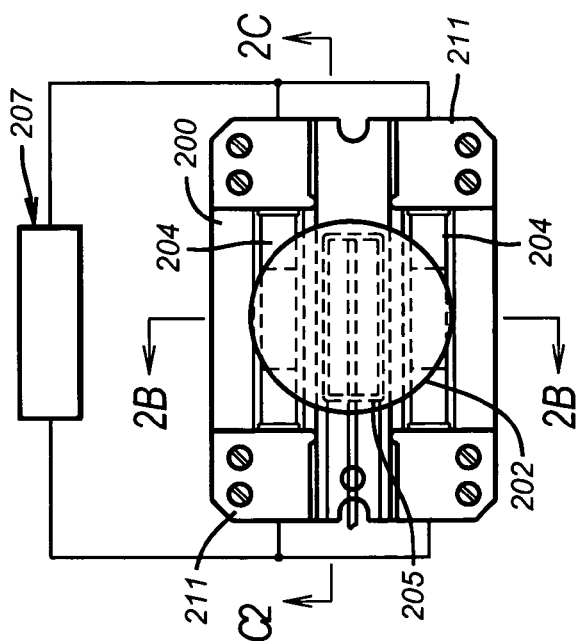
Figure 2C:
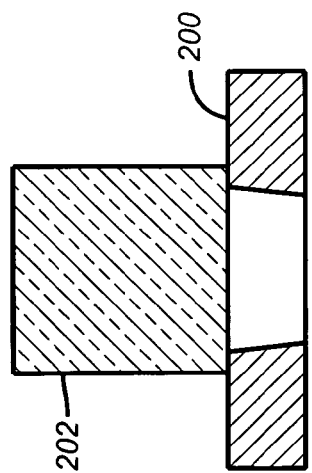

FIG. 2 illustrates the components provided by the present invention to add a ultraviolet light source to a spectral analysis unit, such as the unit shown in FIG. 1. A base plate 200 and screws are provided which serve as a means of attachment to the spectral analysis unit (e.g., SampleViews$^{SM}$). Several bulb or UV LEDs mounts 211 comprise electrical insulating material and screws to hold the mounts in place. These same screws are used to attach the base plate 200 to the spectral analysis unit. An optically clear UV coupler 202 is shown in this diagram to show its positional relationship to two ultraviolet bulbs or LEDs 204 when assembled into the system. The coupler 202 overlaps the light emitting areas of the bulbs 204, thereby confining the path of the UV light to the volumetric region of the optical coupler 202.

Figure 4:
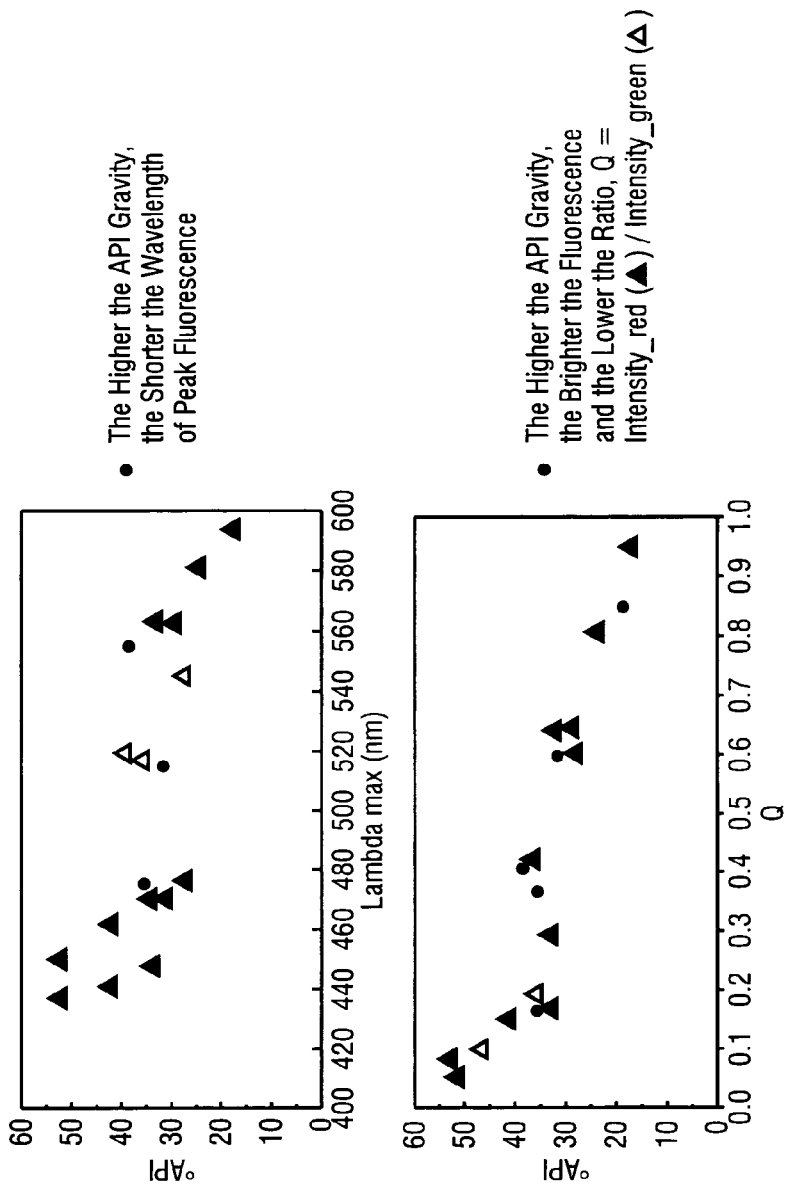
FIG. 4 is a graph of crude oil fluorescence properties showing that the higher the API gravity, the shorter the wavelength of peak fluorescence and the higher the API gravity the brighter the fluorescence and the lower the ratio, Q=intensity of red/intensity of green.

The present invention enables estimating additional crude oil properties downhole because it is known that the brighter and/or bluer the fluorescence the higher the API gravity. It is also known that upon depressurizing a live crude oil, the ratio of blue to green fluorescence will change upon passing below the asphaltene precipitation pressure. Thus, the present invention decompresses a sample while monitoring the blue/green ratio and determines the asphaltene precipitation pressure as that pressure at which the blue green ratio changes from greater than one to less than one. FIG. 4 is a graph of crude oil fluorescence properties showing that the higher the API gravity, the shorter the wavelength of peak fluorescence the brighter the fluorescence and the lower the ratio, Q=intensity of red/intensity of green. (From Geological Survey of Canada, Calgary)

The rectangular window 205 in the center of the base plate 220 provides a pathway through the base plate for a reflected ultra-violet fluorescence response to pass. This pathway enables analysis of other light signals as well (such as due to the tungsten light source) when the UV bulbs or UV LEDs 204 are turned off. A high voltage power supply 207 provides the power to turn the UV bulbs 204 on at 175° C. The UV reflectors 209 are segmented in a manner to aim the reflected light at an angle that will efficiently confine the light within the optically clear UV coupler 202.

Figure 3:
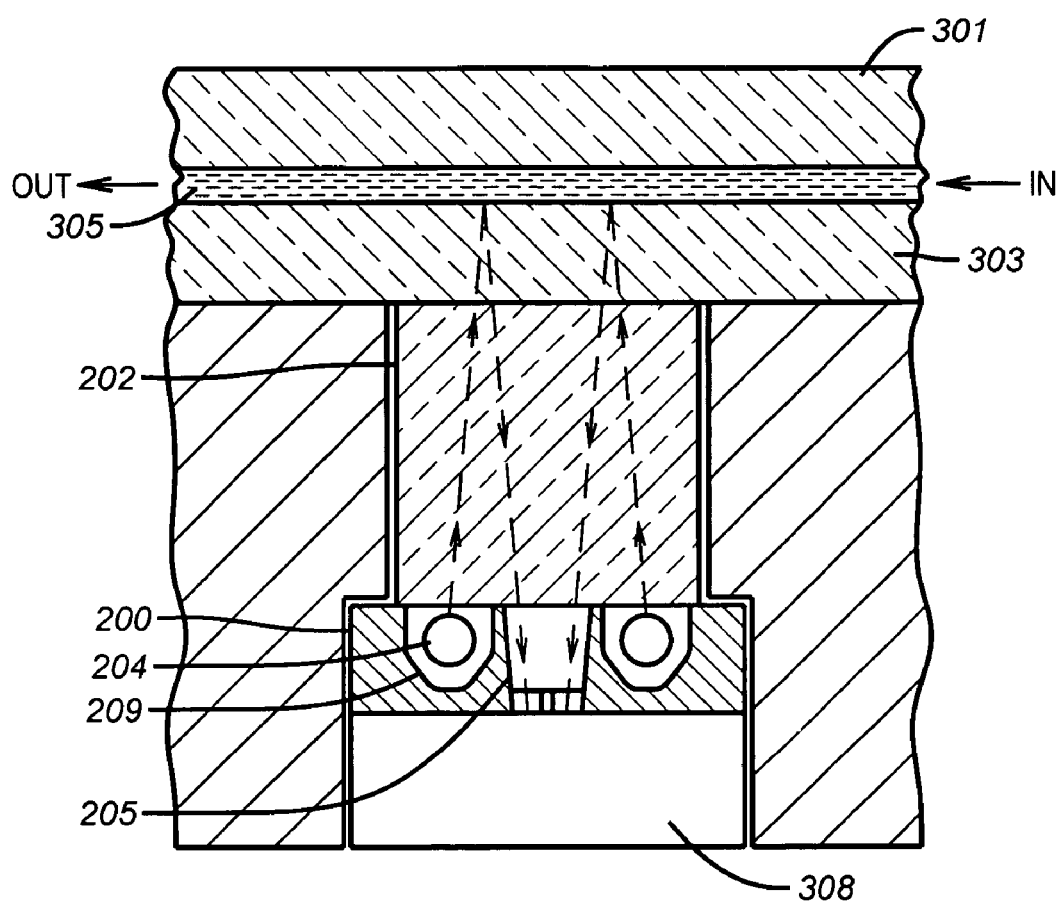
FIG. 3 is a diagram showing installation of the components from FIG. 2.

FIG. 3 illustrates an installation of the components from FIG. 2. The optically clear UV coupler 202, the UV bulbs or UV LEDs 204, the base plate 200, the UV reflection channel 205 are assembled as in FIG. 2. To one side of the optically clear UV coupler 202 lies the UV bulbs or UV LEDs 204, and to the opposite side and resting against it is a fluid containment system comprising two optically clear pressure containment plates, 301 and 303, which are capable of withstanding the high pressure of the formation fluid 305 flowing between them. In a preferred embodiment these containment plates are made of sapphire. The UV coupler 202 and the containment plates are of the materials having substantially the same refractive index, e.g., sapphire, so light can pass from one material to the other without deflection.

Voltage is applied to the bulbs or UV LEDs 204 by the high voltage UV power supply shown in FIG. 2. Both the direct light from the UV bulbs or UV LEDs 204 and the UV light reflected from the UV reflectors 209 are very effectively conveyed to the nearest portion of the formation fluid 305. To concentrate enough UV light on the sapphire window/crude interface, the invention comprises a faceted reflector mirror design 209 along the walls of the cavity of each miniature UV bulb or UV LED and a light-pipe (the optically clear UV coupler) made of a high-refractive index material (sapphire) that captures a large solid angle of UV source light and projects it forward. The reflector mirror improves light intensity by 25% and the light pipe improves light intensity by 235%. This light pipe also collects a large solid angle of the weak fluorescent light, which is forwarded to the detectors.

The formation fluid sample 305 fluoresces when exposed to the ultraviolet light source. The resulting fluorescent radiation from the fluid sample is conveyed back down through the rectangular hole 205 in the base plate and into a spectral analysis unit 308. The reflected fluorescent light provides useful information in the downhole analysis of the formation fluid. Spectral analysis unit 308 also hosts chemometric equations and a neural network for estimating formation fluid purity from fluorescent spectra measurements.

Alternatively a fluorescent tracer is added to the filtrate that fluorescence at a color or wavelength, e.g., red or infrared at which crude oil does not fluorescence. Thus, the present contamination can be determined by ratio of red fluorescence from the OBM tracer to the fluorescence of crude oil.

In a preferred embodiment, the invention monitors crude-oil sample cleanup over time by examining the rising and leveling off of fluorescence over time. For wells drilled with synthetic hydrocarbon-based drilling mud, the invention monitors sample cleanup over time by monitoring fluorescence. The reason is that the base fluids for synthetic mud were designed to be environmentally friendly. Therefore, unlike crude oils, they do not contain the most common fluorescing hydrocarbon compounds, which are aromatics or poly-nuclear aromatics. The synthetic filtrate has little or no fluorescence. Thus, as the crude oil sample cleans up (less filtrate, more crude), the fluorescence increases.

In another embodiment, the invention estimates crude oil properties from fluorescence-ratio models, which are not sensitive to dilution by a generally non-fluorescing liquid, such as the filtrate of synthetic mud. For synthetic mud, whose filtrates have little, if any, fluorescence, the addition of filtrate to a crude oil acts as fluorescence diluents. The present invention provides models that correlate various crude oil properties (e.g., API, Nuclear Magnetic Resonance times T1 and T2, etc.) to ratios of the crude oil's fluorescence at two or more wavelengths. These ratio models are independent of the amount fluorescence-free synthetic mud-filtrate dilution provided that self-absorbance of the excitation and emission wavelengths is kept relatively small.

A processor 308 is provided for implementation of derived chemometric equations and a neural trained network for estimating sample properties from ultraviolet spectra measurements.

The present invention provides fluorescence spectra measurements that can be correlated to the percentages of methane (natural gas), aromatics and other crude oil properties through chemometrics or a neural network. These correlation equations are independent of the crude oil or filtrate involved.

In a preferred embodiment, the present invention uses chemometric derived equations or a neural network to determine the amount of aromatics in a sample analyzed by the present invention based on fluorescence spectra. In known sampling techniques there is no direct measurement of a percent or level of contamination in a sample. The present invention provides a training set of known samples and utilizing chemometrics enables a computer to determine a mathematical expression for a percentage of aromatics based on the spectrum measured for a sample. Using chemometrics eliminates a step in the process of determining the percent of aromatics. Chemometrics also eliminates the need to know what each spectral peak represents and how much a particular peak overlaps another peak. For example, the present invention has been utilized to determine a percent of contaminants based on a chemometric formula derived from known sample having known percentages of aromatics, for example, samples containing 20, 30 and 50 percent aromatics. Typically filtrate does not contain aromatics, thus, the present invention enables direct determination of the percentage of contamination or filtrate in a sample when the percentage of aromatics in the pure crude oil is known or can be estimated. The training set can also be used to train a neural network to predict or determine the percent of aromatics present in a sample. In a preferred embodiment the output of the chemometric calculation and the neural network are compared and a figure of merit value assigned to the output. When both outputs from the chemometric equation and the neural network agree, a high figure of merit of 1.0 is assigned. When the outputs disagree the outputs are averaged and a figure of merit equal to difference between the values divided by the sum of the values subtracted from 1.0 is assigned as a figure of merit.

In a preferred fluorescence spectrometer an approximately 400-nm center-wavelength UV LED is used for excitation and the spectrometer measures how much the crude oil fluorescence in the visible at the colors of Blue, Green, Yellow, Orangey-Red and Deep-Red. We do not report the intensity in channel 1 (Violet=425 nm) because this channel excessively overlaps the band of light produced by our UV LED excitation source. (It's an LED not a laser.) Therefore, considerable light at 425 nm is reflected off the sapphire window and produces signal in channel 1 even when there is only air in the cell.

The present invention provides for a fluorescence reading to measure the fluorescence of the sample independent of any changes in the response of our measuring instrument with temperature or wavelength. To that end, a calibration is provided as follows:

Each calibration correction formula can be thought of as consisting of three factors, Ch_X_Multiplicative_Correction_Factor_at_Temperature_
T=(Correction Factor for Dimming of a UV LED Light
Source, that is Run at Constant Current, as Temperature Increases)*(Correction Factor for Reduction in Photodiode Signal Strength with Increasing Temperature) *(Correction Factor for Differences in Amplifier Gains between Channels, Differences in Photodiode Sensitivity, and Changes in Sensitivity with Temperature)

The first correction factor accounts for the dimming of the UV LED with temperature at constant drive current. Empirically, we found that, for a constant drive current, we lose about 0.47% of the initial (25C) LED intensity for every degree above 25C. Therefore, we multiply each channel's signal by the reciprocal of the fraction of initial UV LED intensity that remains at elevated temperature.

The second correction factor corrects for loss of sensitivity of the photodiodes at elevated temperature. We run the tool in an oven in the lab with air in the cell and the tungsten light bulb at constant brightness. We record a table of values of net signal strength of each channel as a function of temperature. We have a temperature sensor next to the photodiodes so, when running in a well, we use this table to look up a de-rating value based on the temperature and channel number.

The simplest way to correct for the third factor is to use that fact that the black body curve of our tungsten light bulb (that is used in our absorption spectrometer) produces a nearly linear dependence of intensity with wavelength over the visible range of 400–700 nm with red (700 nm) being the brightest. We placed our bulbs in an integrating sphere, ran them at our standard current, and measured their relative irradiance as a function of wavelength over the visible and near-infrared. We used more than one bulb and we used currents slightly above and below our standard current and developed an empirical best fit.

Empircally, we found the black-body relative intensity in arbitrary units to be given by the straight line, $$BBRI = 3.1364*(Wavelength\_in\_nm/1000) - 1.1766$$

Because deep-red (694 nm) is the brightest tungsten bulb channel in the visible, we rescaled the numbers so as to define the BBRI for deep-red as unity as shown in the table below.

We only need the slope because we are not trying to make an absolute irradiance measurement but only a relative irradiance measurement that is consistent across temperature. The tungsten filament is operating at close to 3000 K so there is negligible change in the relative irradiance associated with the raising the temperature of the glass envelope of the bulb to a mere 200 C.

Black Body Relative Irradiance Factors

| | | |
|---|---|---|
| Blue | (Ch_2 = 475 nm) | 0.31319 |
| Green | (Ch_3 = 525 nm) | 0.47001 |
| Yellow | (Ch_4 = 575 nm) | 0.62683 |
| Orangey-Red | (Ch_5 = 632 nm) | 0.80560 |
| Deep-Red | (Ch_6 = 694 nm) | 1.00000 |

Thus, we calculate a correction factor for each channel's signal such that, when running the tungsten bulb with air in the cell, the correction factor multiplied by the raw signal produces a corrected signal which has the ratios of 1 to 0.8 to 0.62 to 0.47 to 0.31 for channels 6, 5, 4, 3, and 2, respectively.

Note that for the absorbance readings, which are based on a ratio, all this extra effort is unnecessary because differences in gain, response, etc. canceled out when ratioing the same channel's reading with air to its reading with crude oil.

For clarity in comparison, the formula for the Ch-6 correction factor is written in the same format that is shown for the other channels. However, for Ch_6 only the first of the three factors, is not equal to one.

Each formula can be thought of as consisting of three factors,

Ch_2_Multiplicative_Correction_Factor_at_T =
   [ 1 / ( 1 − 0.0047 * ( T − 25 ) ) ] *
   (Ch_2_Tungsten_Calibration_Net_Signal_at_25C /
   Ch_2_Tungsten_Calibration_Net_Signal_at_T ) *
   ( 0.31319 * Ch_6_Tungsten_Calibration_Net_Signal_at_T ) /
Ch_2_Tungsten_Calibration_Net_Signal_at_T
Ch_3_Multiplicative_Correction_Factor_at_T =
   [ 1 / ( 1 − 0.0047 * ( T − 25 ) ) ] *
   (Ch_3_Tungsten_Calibration_Net_Signal_at_25C /
   Ch_3_Tungsten_Calibration_Net_Signal_at_T ) *
   ( 0.47001 * Ch_6_Tungsten_Calibration_Net_Signal_at_T ) /
Ch_3_Tungsten_Calibration_Net_Signal_at_T
Ch_4_Multiplicative_Correction_Factor_at_T =
   [ 1 / ( 1 − 0.0047 * ( T − 25 ) ) ] *
   (Ch_4_Tungsten_Calibration_Net_Signal_at_25C /
   Ch_4_Tungsten_Calibration_Net_Signal_at_T ) *
   ( 0.62683 * Ch_6_Tungsten_Calibration_Net_Signal_at_T ) /
Ch_4_Tungsten_Calibration_Net_Signal_at_T
Ch_5_Multiplicative_Correction_Factor_at_T =
   [ 1 / ( 1 − 0.0047 * ( T − 25 ) ) ] *
   (Ch_5_Tungsten_Calibration_Net_Signal_at_25C /
   Ch_5_Tungsten_Calibration_Net_Signal_at_T ) *
   ( 0.8056048 * Ch_6_Tungsten_Calibration_Net_Signal_at_T ) /
Ch_5_Tungsten_Calibration_Net_Signal_at_T
Ch_6_Multiplicative_Correction_Factor_at_T =
   [ 1 / ( 1 − 0.0047 * ( T − 25 ) ) ] *
   (Ch_6_Tungsten_Calibration_Net_Signal_at_25C /
   Ch_6_Tungsten_Calibration_Net_Signal_at_T ) *
   ( 1.0000 * Ch_6_Tungsten_Calibration_Net_Signal_at_T ) /
Ch_6_Tungsten_Calibration_Net_Signal_at_T In one embodiment the inventors have discovered that some UV LEDs perform better than others. SiC has about 4 times better heat transfer (thermal conductivity) than sapphire. AlN has about 10 times the thermal conductivity of sapphire. AlN has about 2 times the thermal conductivity of GaN.

The difference in thermal expansion between AlN and GaN between 1000° C. and room temperature is almost negligible.

The foregoing example of a preferred embodiment is intended for exemplary purposes only and is not intended to limit the scope of the invention, which is defined by the following claims.

What is claimed is:

1. A downhole fluorescence spectrometer for measuring fluorescence of a fluid downhole, comprising:
   a cell for holding the fluid, the cell further comprising a window for passage of light into the fluid;
   an ultraviolet light source for illuminating the fluid; and
   a photo detector having at least two channels in optical communication with the fluid for measuring fluorescence of the fluid,
   wherein the spectrometer utilizes a nearly liner portion of a black body curve to correct signals of the at least two channels.

2. The fluorescence spectrometer of claim 1, wherein a peak fluorescence wave length is measured for determining API gravity.

3. The fluorescence spectrometer of claim 1, wherein the ultraviolet light source is an ultraviolet (UV) light emitting diode (LED) light source.

4. The fluorescence spectrometer of claim 3, wherein the UV LED light source further comprises an array of UV LEDs.

5. The fluorescence spectrometer of claim 3, wherein the spectrometer utilizes a correction factor for correcting dimming of the UV LED Light Source as temperature increases.

6. The fluorescence spectrometer of claim 1, further comprising:
a tracer added to a filtrate for determining sample clean up of the filtrate versus crude oil by detecting a degree of the tracer present in the downhole fluid.

7. The fluorescence spectrometer of claim 6, wherein the tracer further comprises at least one of a red and infrared fluorescent.

8. The fluorescence spectrometer of claim 1, further comprising:
a depressurization device for depressurizing the fluid; and
a processor that determines an asphaltene precipitation pressure based on a blue green fluorescence ratio change over a depressurization curve.

9. The fluorescence spectrometer of claim 1, further comprising:
a correction formula for the photodetector channels comprising a correction factor for raw fluorescence response with respect to temperature.

10. The fluorescence spectrometer of claim 1, wherein the spectrometer corrects for at least one of:
differences in amplifier gains between the at least two channels; dimming of an LED light source with temperature; differences in photo detector sensitivity and; changes in photodetector sensitivity due to temperature.

11. The fluorescence spectrometer of claim 1, further comprising:
a processor configured to monitor fluid cleanup based on fluorescent spectra.

12. A method for measuring fluorescence spectra for a fluid downhole comprising:
illuminating the fluid downhole with an ultraviolet light;
measuring fluorescence of the fluid by a photodetector having at least two channels to determine a parameter of interest for the fluid; and
correcting signals of the at least two channels by utilizing a nearly linear portion of a black body curve over a wavelength range.

13. The method of claim 12, wherein each channel measures fluorescence over a separate wavelength range.

14. The method of claim 12, wherein the ultraviolet light is produced by an ultraviolet (UV) light emitting diode (LED) light source.

15. The method of claim 12, wherein the wavelength range is over a visible range of about 400 nm, to 700 nm.

16. The method of claim 12, further comprising:
adding a tracer to a filtrate for determining fluid clean up of the filtrate versus crude oil by detecting a degree of the tracer present in the fluid.

17. The method of claim 12, wherein the tracer is one of a red and infrared fluorescent.

18. The method of claim 12, further comprising:
depressurizing the fluid; and
determining an asphaltene precipitation pressure based on a blue green fluorescence ratio change over a depressurization curve.

19. The method of claim 12, further comprising:
applying a correction formula for each photodetector channel comprising a correction factor for raw fluorescence response with respect to temperature.

20. The method of claim 12, further comprising:
applying a correction factor for correction for dimming of a UV LED light source as temperature increases.

21. The method of claim 12, wherein correcting signals includes at least one of; differences in amplifier gains between the photodetector channels, differences in photo detector sensitivity and changes in photodetector sensitivity due to temperature.

22. The method of claim 12, further comprising:
monitoring fluid cleanup based on a fluorescent spectra.

23. A computer readable medium containing computer instructions that when executed by a computer perform a method for measuring fluorescence spectra for a fluid downhole comprising:
illuminating the fluid downhole with an ultraviolet light;
measuring fluorescence of the fluid with a photodetector having at least two channels to determine a parameter of interest for the fluid; and
correcting signals of the at least two channels by utilizing a nearly linear portion of a black body curve.

24. The medium of claim 23, further comprising; determining API gravity based on peak fluorescence wavelength of the fluid.

25. The medium of claim 23, further comprising:
providing an ultraviolet (UV) light emitting diode (LED) light source.

26. The medium of claim 23, wherein
providing the UV light source further comprises an array of UV LEDs as a UV LED light source.

27. The medium of claim 23, further comprising:
determining fluid clean up of formation filtrate versus crude oil by detecting a degree of a tracer present in the fluid.

28. The medium of claim 27, wherein the tracer is at least one of a red and infrared fluorescent.

29. The medium of claim 23, further comprising:
determining an asphaltene precipitation pressure based on a blue green fluorescence ratio change over a fluid depressurization curve.

30. The medium of claim 23, further comprising:
applying a correction formula for each photodetector channel comprising a correction factor for raw fluorescence response with respect to temperature.

31. The medium of claim 23, further comprising:
applying a correction factor for correction for dimming of a UV LED Light Source as temperature increases.

32. The medium of claim 23, further comprising:
applying a correction factor differences in amplifier gains between photodetector channels.

33. The medium of claim 23, further comprising:
monitoring fluid cleanup based on the fluorescence spectra.

* * * * *